United States Patent [19]
Waibel

[11] Patent Number: 5,547,582
[45] Date of Patent: *Aug. 20, 1996

[54] PROCESS FOR THE COLLECTION AND TREATMENT OF BIOLOGICAL WASTE

[76] Inventor: Peter J. Waibel, 515 N. 2nd St., New Hyde Park, N.Y. 11040

[ * ] Notice: The term of this patent shall not extend beyond the expiration date of Pat. No. 5,454,953.

[21] Appl. No.: 395,461

[22] Filed: Feb. 28, 1995

Related U.S. Application Data

[62] Division of Ser. No. 68,930, May 28, 1993, Pat. No. 5,454,953.

[51] Int. Cl.$^6$ ........................ C02F 9/00
[52] U.S. Cl. ............... 210/664; 203/10; 203/41; 203/47; 210/669; 210/694
[58] Field of Search ............... 203/10, 41, 47; 210/664, 669, 694, 769, 806

[56] References Cited

U.S. PATENT DOCUMENTS

| | | | |
|---|---|---|---|
| 3,428,556 | 2/1969 | Gunther | 210/664 |
| 3,458,910 | 8/1969 | Ritchey | 27/21 |
| 3,476,570 | 11/1969 | Moustafa | 99/118 |
| 3,549,011 | 12/1970 | Marsh | 210/152 |
| 4,222,857 | 9/1980 | McCarthy | 209/9 |
| 4,251,374 | 2/1981 | Cunningham | 210/454 |
| 4,259,179 | 3/1981 | Marvin | 209/18 |
| 4,338,201 | 7/1982 | Ducasse | 210/771 |
| 4,422,940 | 12/1983 | Cousino et al. | 210/631 |
| 4,430,226 | 2/1984 | Hegde et al. | 203/41 |
| 4,631,133 | 12/1986 | Axelrod | 210/739 |
| 4,655,932 | 4/1987 | Roslonski | 210/709 |
| 4,780,219 | 10/1988 | Witek | 210/786 |
| 4,901,410 | 2/1990 | Fischer et al. | 27/21.1 |
| 4,980,956 | 1/1991 | Fischer et al. | 27/21.1 |
| 4,982,481 | 1/1991 | Deutscher | 27/21.1 |
| 5,037,560 | 8/1991 | Gayman | 210/751 |
| 5,037,561 | 8/1991 | Copeland | 210/769 |
| 5,080,807 | 1/1992 | Carr et al. | 210/772 |
| 5,093,969 | 3/1992 | McGuire | 27/21.1 |
| 5,454,953 | 10/1995 | Waibel | 210/664 |

*Primary Examiner*—Ivars Cintis
*Attorney, Agent, or Firm*—Scully, Scott, Murphy & Presser

[57] ABSTRACT

A multiple-stage process for the collection and treatment of biological waste, and for rendering the biological waste biologically inactive for the safe and economical environmentally non-contaminating disposal thereof. Moreover, also disclosed is an arrangement for the collection and treatment of biological waste utilizing the inventive process, and is especially adapted for the collection and treatment of biological waste which is generated during a surgical or medical procedure implemented on a patient or during an autopsy.

14 Claims, 1 Drawing Sheet

PROCESS FOR THE COLLECTION AND TREATMENT OF BIOLOGICAL WASTE

This is a divisional of application Ser. No. 08/068,930, filed on May 28, 1993, now U.S. Pat. No. 5,454,953.

BACKGROUND OF THE INVENTION

1. Field of the Invention

The present invention relates to a process for the collection and treatment of biological waste, and for rendering the biological waste biologically inactive for the safe and economical environmentally non-contaminating disposal thereof. Moreover, the invention is also directed to an arrangement for the collection and treatment of biological waste utilizing the inventive process, and is especially adapted for the collection and treatment of biological waste which is generated during an embalming procedure implemented on a cadaver, such as a human cadaver.

In general, the disposal of waste, and especially the collection of biological waste and treatment thereof so as to render the biological waste safe for easy, economically viable and environmentally non-contaminating disposal is subject to ever increasing difficulties, which are encountered on a worldwide or universal scale. Hereby, not only is it becoming ever more difficult to obtain adequate landfill or permanent storage space for the disposal of waste, but in addition thereto, particularly biological waste must be collected and treated in a manner as to be resultingly easily rendered biologically sterile and safe in order to conform with more stringent environmental regulations and standards currently being promulgated; for example, as proposed by the Federal/EPA, local and municipal ordinances and the like.

Among various problems which have been addressed by the waste treatment/disposal technology is the rendering of biological waste environmentally non-contaminating; in effect, to essentially prevent such collected biological and potentially toxic waste from polluting ground water and soil endangering the life and health of the population; for instance, when such waste contains one or more radioactive, toxic or biologically hazardous constituents.

Attempts are currently being made to render biological waste disposable in an environmentally safe or non-contaminating manner; however, these efforts have not been specifically directed towards obviating the difficulties encountered in collecting and treating biological waste generated during embalming procedures carried out in undertaking establishments, that obtained during surgical operating procedures or during the autopsying or dissection of cadavers, in which considerable biological fluid components, such as bloods and the like must be flushed from the cadaver in conjunction with possibly present embalming and processing chemicals, such as formaldehyde and the like. At this time, generally such biologically active or contaminated fluids are flushed into a drain and normally conducted into municipal sewage or drainage systems, and with solids components contained in the fluid or blood, such as blood clots, body parts, tissue, fats and other chemicals frequently being flushed into the drainage or sewage system while entrained in the fluids. This method of disposing of biological waste has led to potentially serious and hazardous, health-endangering contamination of ground water or soil due to seepage of the waste liquids and necessitated the installation and maintenance of highly expensive waste treatment plants in various municipalities and geographic locales.

2. Discussion of the Prior Art

Although various systems have been designed and developed for the treatment and disposal of biological waste, none of these have been able to facilitate an easy, safe and environmentally non-contaminating disposal adapted to extensively reduce costs and the volumetric extent of the treated waste, while rendering the latter biologically inactive and safe for sterile disposal, and concurrently eliminating or reducing the need for large waste treatment systems, storage and disposal sites or landfills.

Among various arrangements and methods for the treatment of biological or toxic waste, especially biological waste incorporating solid and liquid constituents; for instance, such as may be encountered during the embalming of cadavers, consideration must be given to potentially applicable types of waste disposal technology.

Gayman U.S. Pat. No. 5,037,560 discloses a sludge treatment process wherein sludge including toxic materials is conducted through a series of heating stations, such as microwave ovens, which will essentially evaporate and separate out the liquid portion of the sludge and enable the resultant dried components to be conveyed into suitable containments for permanent storage.

Carr, et al. U.S. Pat. No. 5,080,807 discloses a continuous particle separation process incorporating a plurality of steps in which particulate material is separated in sequential filtering stages from a fluid so as to facilitate the classification of the various components and separate disposal thereof.

McGuire U.S. Pat. No. 5,093,969 discloses a self-contained viscera treatment unit in which liquids may be drained from viscera which is removed from a cadaver, and the viscera stored until subsequently replaced in the cadaver or human remains for burial, cremation or other suitable disposal. There is no disclosure of providing an installation or process for rendering waste biologically safe for environmentally non-contaminating disposal.

Witek U.S. Pat. No. 4,780,219 discloses a system for filtering suspended solids from a liquid in which the solids are entrained, whereby the solids-containing liquid is passed through a filtering unit such as a filter bag, which enables the solids to be retained therein and separated from the liquid being discharged therethrough.

Copeland U.S. Pat. No. 5,037,561 discloses a method for drying biological sludge in which a filtering system employs heating components adapted to evaporate liquid constituents of the sludge so as to enable the disposal of dried residual combustible portions in a combustion system.

Ritchey U.S. Pat. No. 3,458,910 discloses an apparatus and method for handling and embalming viscera in which the latter are placed into a liquid-impervious liner contained within a bucket while a cadaver is being prepared. Thereafter, the liner is sealed and replaced together with its contents in the cadaver for burial or cremation. There is no disclosure of a system analogous to that contemplated by the invention for the collection and treatment of biological waste in order to render it biologically inactive for environmentally-safe disposal thereof.

Fischer, et al. U.S. Pat. Nos. 4,901,410 and 4,980,956 each disclose an anatomical preparation station which enables embalming fluids, body tissues and biological discharges from a cadaver to flow through a drain hole located in a cadaver preparation table into a sink so as to be admixed with a continuous water flush for subsequent conduction into a municipal drainage or sewage system. There is no provision in these disclosures for rendering such biological waste biologically inactive and safe for the disposal thereof in accordance with municipal and federal environmental regulations which are concurrently in force or intended to be promulgated in order to protect the environment and population.

Finally, Deutscher U.S. Pat. No. 4,982,481 discloses an embalming system and method in which embalming fluid and other biological liquid waste is drained from a cadaver into a disposable container which is subsequently arrangeable with its contents in a coffin in conjunction with the burial with the other remains of the cadaver. However, as in the above-mentioned publications, there is no consideration given to the aspects of rendering such biological waste biologically inactive for the environmentally safe disposal thereof, inasmuch as it is conceivable that over an extended period of time, such untreated biological waste may leak into the ground upon the rotting and resultant breach of the coffin, whereby the waste when mixed with ground moisture or rain water, may potentially contaminate the environment.

SUMMARY OF THE INVENTION

Accordingly, it is a primary aspect of the present invention to provide a process and an arrangement for the collection and treatment of biological waste, and for rendering the biological waste biologically inactive so as to enable the environmentally non-contaminating disposal thereof, in which the biological waste is initially constituted of organic solids constituents entrained in a liquid.

In particular, the inventive process and arrangement for the collection and treatment of biological waste are each well suited for use in conjunction with the current procedures employed in the embalming of human remains or cadavers, wherein, heretofore, body fluids, incorporating tissue, fats, blood clots and water, and inclusive of formaldehyde and embalming fluid have generally been flushed through a drain into a municipal sewage system, tending to contaminate the eco-system or environment, such as the ground water and subsoil.

In order to overcome or ameliorate the disadvantages which are encountered in the state-of-the-art relative to the safe and economical collection and treatment of biological waste, the present invention contemplates the provision of a multi-stage waste treatment process and arrangement for implementation thereof, wherein initially, the obtained biological waste; for instance, during an embalming process carried out on human remains or a cadaver, is permitted to drain into a filter which may be a liquid-permeable depth filter or filter bag supported within an liquid-impervious housing, the latter of which will permit the major portion of the liquid from the waste to pass out through the filter so as to discharge from an outlet of the housing into a closed collection vessel, while the major portion of solids constituents, such as tissue, fats, blood clots and the like which were entrained in the liquid are retained in the filter.

In the collection vessel, which is lined with a liquid-impervious, heat-resistant liner in the shape of an upwardly opening bag, the primarily liquid biological waste is heated to a temperature adequate to convert the liquid into a vapor or steam, which is conveyed from the vessel to an external liquid pump converting the discharged heated vapor into a liquid state, and with any residual solids which previously remained entrained in the liquid when passed through the filter into the collection vessel, such as residual blood, proteins, fats and the like being retained and collected within the liquid-impervious and heat-resistant liner supported within the collection vessel.

The liquid discharged from the liquid pump, which is derived from the condensed or liquefied vapor, is then conveyed through a suitable liquid or water discharge conduit into a resin bed filter, such as a filter cartridge, which separates out and precipitates any light organics, for example, formaldehyde or alcohol remaining in the liquid, and thereby enables the discharging of an essentially purified liquid which is primarily constituted of clean water, into the municipal drainage or sewage system.

The solids which remain in the initial filter bag or depth filter, and the residual solids which have collected in the liner of the collection vessel upon vaporization of the waste liquid, may then be removed from the arrangement while still respectively contained in the filter and liner and sanitarily collected for the economical non-polluting disposal thereof, such as by incineration. Hereby, inasmuch as the obtained solids and the filter and liner are all organic in nature, their collective incineration will only produce non-toxic emissions.

The foregoing clearly evidences that the advantages of the inventive process and arrangement, among others, consist of the safe and environmentally sound non-polluting disposal of biological waste, especially embalming waste produced during embalming procedures carried out on cadavers; a considerable decrease in treating costs and in the volume of the biological waste which is being disposed of so as to render the entire process and attendant arrangement simple and highly economical; rendering the waste biologically inactive and environmentally safe so as to meet all local municipal and federal or national government ordinances and regulations; reducing the need for large-scale waste recovery, storage and disposal systems including a reduced demand on landfill; and the provision of a novel and unique self-contained biological and embalming waste treatment system which is essentially portable and can be employed at any suitable location, such as at various undertaking establishments, hospitals and at locations where autopsies are conducted on cadavers.

Accordingly, it is a primary object of the present invention to provide a novel process for the collection and treatment of biological waste, and for rendering the biological waste biologically inactive to enable the ecologically and environmentally non-contaminating disposal thereof.

Another object of the present invention is to provide a process as described herein, wherein the process is utilized for the collection, treatment and rendering biologically inactive of biological and embalming waste obtained during an embalming procedure which is implemented on cadavers or human remains.

Still another object of the present invention is to provide a novel process for the collection and treatment of biological waste as described, in which liquid and solids constituents of the biological waste are efficiently separated in a plurality of steps enabling the environmentally safe disposal of the solids constituents while rendering the liquid constituent biologically inactive so as to eventually produce essentially purified water which can be readily disposed of in a municipal or public drainage or sewage system.

A further object of the present invention is to provide all arrangement for implementing the process of collecting, treating and biologically rendering safe biological waste, in which such arrangement is inexpensive and may be portable in nature so as to be able to be employed at a plurality of locations.

BRIEF DESCRIPTION OF THE DRAWINGS

Reference may now be had to the following detailed description of an exemplary embodiment of the invention, taken in conjunction with the accompanying drawings, in which.

DETAILED DESCRIPTION

Figure 1:
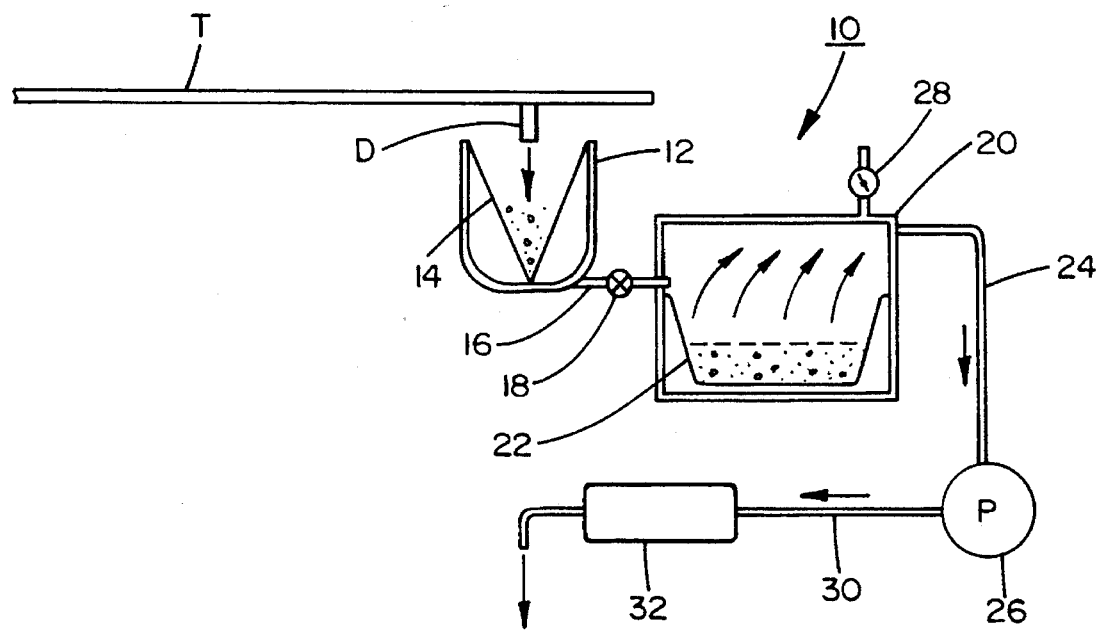
FIG. 1 illustrates a generally schematic representation of an arrangement for the collection and treatment of biological waste so as to render the biological waste safely disposable in an environmentally non-contaminating manner.

Referring now more specifically to the drawings, and especially the generally schematically illustrated arrangement shown in FIG. 1, a biological waste collection and treatment arrangement 10 includes a bucket or bowl-shaped housing 12 constituted of a liquid or fluid-impervious material of sterilizable quality, such as stainless steel or the like, wherein the upper end of the housing 12 is open so as to receive therein a liquid-permeable depth filter or filter bag 14, with the filter being preferably constituted of a polypropylene material.

The arrangement 10 is adapted to be positioned adjacent or beneath a biological waste producing station; for example, an embalming table T for cadavers or human remains, which has a drain D located above the opening of the housing 12 so as to enable the biological waste to pass into the drain and to flow downwardly into the filter 14.

In essence, when the arrangement 10 is utilized for the collection and treatment of biological waste received from an embalming procedure imparted to a cadaver or human remains, the flow of the biological waste into the filter 14 consists of a liquid and entrained solids mixture essentially constituted of body fluids, tissue, fats, blood clots, formaldehyde, embalming fluid and water. As the biological waste is conveyed into the filter 14, the liquid portion of the waste passes therethrough and is discharged through an outlet conduit 16 located proximate the lower end of housing 12, and which has a suitable shut-off valve 18 located therein, with at least the major portion of the solids from the waste being restrained within the filter 14.

The outlet conduit 16 causes the discharged liquid portion of the biological waste to be conveyed into the upper region of a closed collection vessel 20 which has a heat-resistant and liquid-impervious liner 22 mounted therein, with the liner preferably being constituted of a polyethylene material.

A heating arrangement, such as electrical heating coils or the like (not shown), is provided in the collection vessel 20 so as to raise the temperature of the atmosphere therein to above the boiling or vaporization point of the waste liquid which has been conducted into the liner 22 from the outlet conduit 16 of housing 12, causing the resultingly vaporized liquid to be discharged through a discharge conduit 24 communicating with the upper region of the collection vessel 20 and into a suitable pump 26, whereby such pump may be a liquid ring pump, as is known in the technology, and in which the vapor is condensed into a liquid state, consisting primarily of water. Furthermore, the upper end of the collection vessel 20 may be equipped with a suitable pressure-relief vent or vacuum breaker 28 which will prevent the build-up of excess pressure in the collection vessel 20 during the vaporization of the liquid waste being heated therein.

The discharge of the vaporized liquid or steam from the collection vessel 20 will cause any residual solids having passed through filter 14 to be separated therefrom so as to settle and remain in the liner 22, such residual solids consisting essentially of residual blood, proteins, fats, lipids, minute quantities of bacteria and virus-contaminated water and embalming chemicals.

The water or liquid which is conducted through the liquid pump from 26 from the vapors being condensed therein is conducted through a water discharge conduit 30 into a resin bed filter 32, which is adapted to remove or separate out any light organics, for example, such as formaldehyde and alcohol contained in the liquid and restrain and/or embed these light organics in the filter 32 while permitting the discharge therefrom of the substantially purified liquid, essentially consisting of water, into a suitable sink or drain leading to a municipal drainage or sewage system, or other suitable disposal sites.

The bed filter 32 may be constituted of a cartridge of activated charcoal and/or carbon, a resin or mixed resin, or of a molecular sieve, and may be periodically removed and cleansed or recharged, or replaced by another clean filter cartridge.

In order to complete the disposal of the collected and treated biological waste, upon completion, for example, of a particular embalming procedure on a cadaver or human remains, after the liquid portion of the biological waste has been discharged from the arrangement 10 through the resin bed filter 32 into a drain or discharge, the filter bag or depth filter 14 containing the biological waste solids may be removed from the housing 12, and the liquid-impervious liner 22 with any residual solids contained therein may also be removed from the collection vessel 20, and with both the filter 14 and liner 21 together with their contents being conveyed for environmentally safe disposal thereof, such as by incineration. Hereby, inasmuch as the deliquefied waste solids, the filter 14 and the liner 22 are of materials of an organic nature, high-efficiency incineration thereof will only produce non-toxic emissions so as not to contaminate the environment. Similarly, the treated liquid portion of the biological which is discharged into a municipal drainage or sewage system from the filter bed 32 is also essentially a decontaminated and purified liquid, primarily clean water, and will not in any manner contaminate the ground water or soil so as to also provide for an environmentally safe disposal thereof.

I as much as the basic components of the arrangement 10, such as the housing 12, the collection vessel 20, the pump 26 and the resin bed filter 32 and the various conduits are essentially constituted of stainless steel or similar easily cleanable and sterilizable materials, it is expedient to be able to cleanse and sterilize these components by means of suitable cleaning solutions so as to prepare the arrangement for use in a subsequent embalming or waste-treating process.

Figure 2:
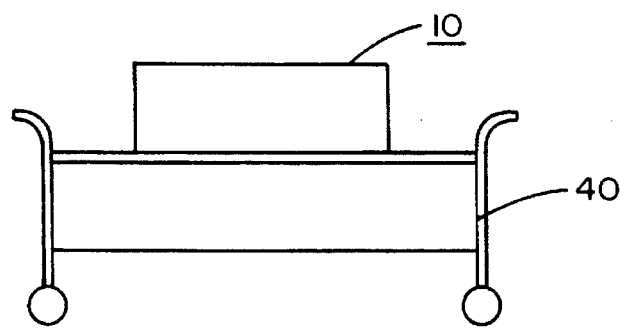
FIG. 2 illustrates, generally diagrammatically, a portable installation incorporating the inventive arrangement for use thereof in connection with embalming stations.

Furthermore, as schematically illustrated in FIG. 2 of the drawings, the entire arrangement 10 may be constructed compactly and mounted on a suitable portable platform or mobile cart 40 so as to be transportable from one location to another. Furthermore, suitable electrical connections (not shown) may also be provided so as to be able to connect components, such as heating elements for the collection vessel 20 and power for pump 26, to standard residential or commercial electrical outlets.

From the foregoing, it clearly becomes apparent that the invention is directed to a novel and highly effective process and arrangement for the collection and treatment of biological waste, which will enable the highly economical applications thereof to numerous uses. Although described particularly in connection with an embalming process, such as is currently employed in undertaking establishments, it is, of course, readily apparent that the arrangement may also be utilized in various clinics and hospitals for the purpose of disposing of biological waste and/or organics obtained during surgery and in the dissecting of cadavers during autopsies and for medical research purposes, both in connection with human remains and animal cadavers.

While there has been shown and described what is considered to be a preferred embodiment of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A process for the collection and treatment of biological waste, and for rendering the biological waste biologically inactive for the environmentally non-contaminating disposal thereof, said biological waste being obtained from a surgical or medical procedure implemented on a patient or an autopsy and comprises body fluids, tissue, fats, blood clots and water, wherein said biological waste is initially constituted of organic solid constituents entrained in liquid; said process comprising the steps of:

(a) conducting a quantity of the biological waste into a liquid-permeable filter arranged within a fluid-impervious housing, discharging at least a major portion of the liquid of said waste which is passed through said filter into an outlet of said housing while retaining solids from said waste within said filter;

(b) conducting the discharged liquid portion of said waste and any residual solids contained therein from said outlet into an enclosed collection vessel; heating the interior of said collection vessel so as to vaporize said liquid portion; discharging said vaporized liquid portion from said collection vessel while retaining said residual solids in said collection vessel;

(c) liquefying said vaporized liquid portion upon discharge from said collection vessel into a liquid essentially constituted of water;

(d) conducting said liquid through a bed filter so as to separate therefrom any residual light organic materials and embedding said organic materials in said bed filter so as to purify said liquid;

(e) and draining the purified liquid from said bed filter.

2. A process as claimed in claim 1, wherein said liquid-permeable filter in said housing comprises a disposable polypropylene depth filter.

3. A process as claimed in claim 1, wherein said liquid-permeable filter in said housing comprises a disposable polypropylene bag filter.

4. A process as claimed in claim 1, wherein subsequent to the discharge of the liquid portion of the waste from said housing, said liquid-permeable filter is removed from said housing with the deliquefied separated waste solids contained therein for the environmentally non-contaminating disposal thereof.

5. A process as claimed in claim 4, wherein said filter and therein contained deliquefied waste solids are disposed of by incineration.

6. A process as claimed in claim 1, wherein said collection vessel is lined with a liquid-impervious, heat-resistent liner for receiving the liquid portion and any therein entrained residual solids of the biological waste passed through said filter and discharged from said housing, comprising removing said liner and the residual solids contained therein from said collection vessel, subsequent to vaporization and separation therefrom of the liquid portion for the environmentally non-contaminating disposal thereof.

7. A process as claimed in claim 6, wherein said liner and therein contained deliquefied residual waste solids are disposed of by incineration.

8. A process as claimed in claim 7, wherein said liner is constituted from polyethylene.

9. A process as claimed in claim 1, wherein said bed filter comprises a replaceable filter cartridge.

10. A process as claimed in claim 1, wherein said purified liquid is dischargeable from said bed filter into a municipal drainage or sewage system.

11. A process as claimed in claim 1, wherein said deliquefied residual solids remaining in said collection vessel subsequent to vaporization and separation therefrom of the liquid portion of said biological waste comprise constituents containing at least one or more of residual blood, proteins, fats and residual quantities of liquid containing bacteria and viral contaminants.

12. A process as claimed in claim 1, wherein said bed filter comprises an activated charcoal and carbon filter.

13. A process as claimed in claim 1, wherein said bed filter comprises a resin filter.

14. A process as claimed in claim 1, wherein said bed filter comprises a molecular sieve.

\* \* \* \* \*